United States Patent
Zhu et al.

(10) Patent No.: US 9,937,122 B2
(45) Date of Patent: Apr. 10, 2018

(54) PALONOSETRON ORAL TRANSMUCOSAL FILM OR PATCH

(71) Applicant: LP PHARMACEUTICAL (XIAMEN) CO., LTD., Xiamen (CN)

(72) Inventors: Haijian Zhu, Xiamen (CN); Rongbin Ling, Xiamen (CN); Qing Luo, Xiamen (CN); Ying Ye, Xiamen (CN)

(73) Assignee: XIAMEN LP PHARMACEUTICAL CO., LTD., Xiamen (CN)

( * ) Notice: Subject to any disclaimer, the term of this patent is extended or adjusted under 35 U.S.C. 154(b) by 0 days.

(21) Appl. No.: 15/208,412

(22) Filed: Jul. 12, 2016

(65) Prior Publication Data

US 2017/0367969 A1    Dec. 28, 2017

(30) Foreign Application Priority Data

Jun. 28, 2016   (CN) .......................... 2016 1 0487192

(51) Int. Cl.

| | |
|---|---|
| *A61K 31/473* | (2006.01) |
| *A61K 9/00* | (2006.01) |
| *A61K 9/70* | (2006.01) |
| *A61K 47/46* | (2006.01) |
| *A61K 47/26* | (2006.01) |
| *A61K 47/36* | (2006.01) |
| *A61K 47/38* | (2006.01) |
| *A61K 47/10* | (2017.01) |
| *A61K 47/32* | (2006.01) |

(52) U.S. Cl.
CPC ............ *A61K 9/006* (2013.01); *A61K 9/7007* (2013.01); *A61K 31/473* (2013.01); *A61K 47/10* (2013.01); *A61K 47/26* (2013.01); *A61K 47/32* (2013.01); *A61K 47/36* (2013.01); *A61K 47/38* (2013.01); *A61K 47/46* (2013.01)

(58) Field of Classification Search
CPC .... A61K 31/473; A61K 9/006; A61K 9/7007; A61K 47/10; A61K 47/32; A61K 47/36; A61K 47/38; A61K 47/26; A61K 47/46
See application file for complete search history.

(56) References Cited

U.S. PATENT DOCUMENTS

| | | | |
|---|---|---|---|
| 8,147,866 B2 | 4/2012 | Finn et al. | |
| 9,301,948 B2 | 4/2016 | Zerbe et al. | |
| 2007/0207192 A1* | 9/2007 | Holl ...................... | A61K 9/006 424/449 |
| 2012/0076921 A1* | 3/2012 | Myers .................... | A61K 31/47 427/2.14 |

FOREIGN PATENT DOCUMENTS

CN   102652739   9/2012

* cited by examiner

*Primary Examiner* — Sarah Pihonak

(74) *Attorney, Agent, or Firm* — Perkins Coie LLP; Viola T. Kung

(57) ABSTRACT

The present invention provides a pharmaceutical composition for delivering palonosetron through the buccal mucosa or sublingual mucosa. The pharmaceutical composition comprises 0.05-35% (w/w) of palonosetron, 40-90% of a film forming agent, 1-10% (w/w) of a plasticizer, 5-25% (w/v) of an adhesive agent, and 0.1-5% of a penetration enhancing agent. A preferred plasticizer is a polysorbate. A preferred adhesive agent is polyvinylpyrrolidone or carboxymethylcellulose. A preferred penetration enhancing agent is peppermint oil or menthol.

14 Claims, No Drawings

PALONOSETRON ORAL TRANSMUCOSAL FILM OR PATCH

This application claims the priority of Chinese Application No. 201610487192.2, filed on Jun. 28, 2016; which is incorporated herein by reference in its entirety.

FIELD OF INVENTION

The present invention relates to a pharmaceutical composition in a film or patch format for delivering palonosetron through the buccal mucosa or sublingual mucosa.

BACKGROUND OF THE INVENTION

Cancer has become the first threat to human health. Chemotherapy is the major means for treating neoplastic diseases. While the nausea and emesis is one of the most common side effects from anti-cancer chemotherapy. Severe emesis can lead to dehydration, electrolyte imbalance, weakness, and even the patient refused treatment. Currently the main use of antiemetic granisetron is 5-HT3 antagonist.

Palonosetron has recently emerged as a highly efficacious anti-nauseant and anti-emetic during anti-cancer chemotherapy. Palonosetron is selective, showing a high affinity as an antagonist for the 5-hydroxyltry ptamine 3 receptor precursor (5-HT3 receptor), and has the advantage of high efficacy, long duration, tolerability and fewer side-effect when compared with the traditional 5-HT3 receptors.

Palonosetron is sold as a sterile injectable liquid in the United States in July 2003 as ALOXI® by MGI Pharma and Helsinn Healthcare SA. After listing, it soon became the first choice for prevention of nausea and vomiting. At present, the listed products also have capsules and sprays. Despite numerous clinical benefits and advantages of this intravenous formulation, it is generally recognized that injection drug delivery systems present special problems with respect to storage life and stability of the active agent. Injection is also inconvenient when self-administered, and has an increased risk of contamination and human error. Oral administration may induce patient nausea, which resulting in vomiting out chemotherapeutic agents and reducing the efficacy of the chemotherapeutic agent. Further, some patients cannot use capsules due to difficulty swallowing.

There exists a need for a method and a composition for delivering palonosetron with improved bioavailability and fewer side effects.

DETAILED DESCRIPTION OF THE INVENTION

In order to meet the clinical requirements of prevention of the nausea and emesis, the present invention provides a palonosetron oral transmucosal film or patch which is a non-invasive, painless and convenient. When the film or patch is applied buccally or sublingually to a subject, palonosetron is almost completely absorbed at the mucous membrane of the oral cavity in the applied region and then enters into the bloodstream, which helps to avoid drug vomiting and reducing drug bioavailability.

The inventors have discovered a pharmaceutical composition suitable for buccal or sublingual administration of palonosetron with improved bioavailability. In one embodiment, the pharmaceutical composition is in an oral film or patch format. The palonosetron oral transmucosal film or patch of the present invention is essentially uniform in thickness and color, without bubbles, and with good stability under common storage conditions. The buccal transmucosal film of the present invention quickly adheres to the buccal mucosa, promotes drug absorption, and has high bioavailability. The pharmaceutical composition of the present invention makes it possible to administer palonosetron buccally or sublingually by a transmembrane route. Buccal epithelium is a relatively permeable non-keratinized tissue; where blood vessels drain directly into the jugular vein.

The pharmaceutical composition of the present invention is administered buccally or sublingually by placing the pharmaceutical composition in the mouth of a subject, either under the tongue (sublingual) or between the gum and the cheek (buccal). The pharmaceutical compositions are absorbed through the mucous membranes of the mouth and enter into the bloodstream. Buccal or sublingual administration of the present pharmaceutical composition is effective, because buccally or sublingually bypasses the digestive system and is absorbed into the bloodstream in minutes.

The pharmaceutical composition provides a good water solubility and typically is dissolved in water completely in less than 5 minutes, preferably less than 3, 2, or 1 minutes. The pharmaceutical composition of the present invention is designed to achieve a desired palonosetron absorption profile and peak blood level and to provide a favorable pharmacokinetic profile with good bioavailability. The pharmaceutical composition is preferably in a film format, in a weight of about 10-80 mg, preferably about 20-50 mg.

"About" when used in this application, refers to ±10% of the recited value.

Unless otherwise specified, % used in this application refers to weight by weight %.

The present invention is directed to a pharmaceutical composition comprising 0.005-35% (w/w) of palonosetron, 40-90% of one or more film forming agents, 1-10% (w/w) of one or more plasticizers, 5-25% (w/v) of one or more adhesive agents, and 0.1-5% of one or more penetration enhancing agents.

The active ingredient in the pharmaceutical composition is palonosetron or a pharmaceutically acceptable salt thereof, e.g., palonosetron hydrochloride. The amount of palonosetron in the pharmaceutical composition of the present invention in general is about 0.005-28 mg, preferably about 0.05-20 mg, or about 0.1-15 mg. The concentration of palonosetron in the pharmaceutical composition of the present invention is in general 0.005-35%, preferably 0.05-35%, 0.1-35%, 0.2-30%, 0.5-25%, 1-25%, or 1-20% (w/w).

For administration by mucosa and sublingual mucosal drug delivery, a good film or patch should be soft, and when it is exposed to saliva, it should quickly release the drug. The film forming material should be compatible to palonosetron. Film-forming materials useful in the present invention include hydroxypropyl cellulose, hypromellose, sodium carboxymethyl cellulose, xanthan gum, pectin, polyvinyl pyrrolidone, -polyethylene oxide, sodium alginate, and chitosan. Preferred film forming materials include low viscosity hydroxypropyl cellulose and a mixture of hydroxypropyl cellulose and hypromellose. The viscosity of hydroxypropyl cellulose is from about 300 to 600 mPa·s (millipascal·second) at 10% concentration. The viscosity of hypromellose is about 3-50 mPa·s at 2% concentration. The amount of film forming materials is about 40-90% (w/w), or 45-90%, or 50-90% (w/w). The film formed with the said film forming materials has good flexibility and adhesion.

Generally, flexibility is an important factor to the quality of a film or patch. In order to improve the flexibility of the film and to improve the smoothness of the film appearance, the inventor screened different plasticizers. Plasticizer agents suitable in the present invention include polysorbate 80, polysorbate 20, polyethylene glycol, propylene glycol, hexylene glycol and polypropylene glycol. Other plasticizers may result in forming the films being less flexible and being brittle. The concentration of one or more plasticizer agents in the pharmaceutical composition of the present invention is in general 0.5-10%, preferably 1-10%, 1-9%, or 1-8% (w/w).

Bioavailability is affected by the rate of a drug absorbed through the oral mucosa and the time the film adhering to the oral mucosa. In order to improve the drug bioavailability, the inventors screened a variety of adhesive agents and penetration enhancers. The inventors have discovered that different adhesives have different effects on the drug bioavailability; some adhesives suppress drug dissolution and reduce drug bioavailability. Adhesive agents useful in the present invention include one or more ingredients as follows: polyvinyl pyrrolidone (PVP), sodium carboxymethyl cellulose (CMC), poly aspartic acid, polyglutamic acid, phenylacetic acid, polycarbophil, carbomer, carbopol, dextran sulfate, and chondroitin sulfate. Polyvinyl pyrrolidone and sodium carboxymethyl cellulose are preferred adhesive agents; their viscosity is about 20-300 mPa·s at 2%. The adhesive in the pharmaceutical composition is in an amount from about 2% to 30% (w/w), and preferably 5-25% (w/w). The adhesives used in the present invention provide a good adhesion, and do not negatively impact on drug dissolution. When the amount of the adhesive in the film is greater than 31%, for example 40%, it may improve the adhesion properties of the film, but it may decrease the amount of drug released from the film or patch, and thus may lower bioavailability.

The absorption rate of the drug through the buccal mucosa is another factor contributing to the bioavailability of the film or patch. In order to increase the absorption rate of the drug through the mucosa, one or more penetration enhancers are added to the pharmaceutical compositions. Penetration enhancers useful for the present invention include one or more ingredients as follows: peppermint oil, menthol, propylene glycol, poloxamer, sodium deoxycholate, sodium lauryl sulfate, eucalyptus oil, oleinic acid, polysorbate, sorbitan monolaurate, glyceryl laurate, and azone. Preferred penetration enhancers include peppermint oil and menthol, which improve the bioavailability of the drug to more than 80%. The concentration of one or more penetration enhancers in the pharmaceutical composition of the present invention is in general 0.1-5%, preferably 0.5-2% (w/w).

Due to the bitter taste of palonosetron, the pharmaceutical compositions optionally contain a flavoring or taste masking agent to decrease its bitterness and increase patient compliance. The flavoring agent may include one or more ingredients as follows: sucralose, sucrose, glucose, sodium saccharin, fructose, xylitol, stevia, aspartame, neotame and acesulfame potassium. Sucralose is a preferred flavoring agent for the present invention. The amount of a flavoring agent in the composition is about 0.01-2.5%, preferably about 0.05-1.5%, or 0.1-1%.

The pharmaceutical composition of the present invention has the following advantages. The palonosetron film or patch is completely dissolved and absorbed to the membrane of the oral cavity so that a patient can easily receive the palonosetron. The palonosetron film or patch can be taken without water, which is particularly suitable for patients who undergo chemotherapy and possibly vomit if drinking water. The palonosetron film or patch can quickly release a palonosetron and has a bioavailability at least 50%, preferably at least 60%, 70%, or 80%.

The present invention provides a method for preparing palonosetron oral transmucosal film. The method comprises the following steps:

a. adding palonosetron, the film-forming materials, the plasticizers, the adhesive agents, the penetration enhancers, and optionally flavoring agents in a vial containing an aqueous organic solvent, stirring the vial until it is completely dissolved, and removing any air bubbles to form a film solution;

b. coating the film solution of (a) on a substrate and drying the film solution to form a film; and c. removing the film from the substrate and optionally cutting it into a suitable size and shape.

In step (a), an appropriate solvent is an aqueous solvent comprising ethanol, isopropanol, ethyl acetate, and/or t-butanol in water. A preferred solvent is an ethanol aqueous solution comprising 15-45%, or 20-40% ethanol, which can completely dissolve all the materials in the solution to form a homogeneous solution, which can also reduce the drying temperature and accelerate drying speed. When the amount of the ethanol in the ethanol aqueous solution is greater than 46%, for example 50%, the solution cannot completely dissolve all the materials in the solution to form a homogeneous solution, and the resulting film shows many particles. In one embodiment, the film forming solution contains 10% of the pharmaceutical composition as described above and 90% of an aqueous solution containing 15-45% of an ethanol solution. The present invention provides a aqueous film forming solution comprising about 10% of the pharmaceutical composition of as described above, about 10-40% ethanol, and water.

In step (b), the drying temperature is about 40°–100° C., preferably about 55-80° C. In one embodiment, the defoamed film solution of (a) is evenly coated on a conveyor belt which is moved to a hot air drying oven to form a film.

In step (c), after the film is removed from the substrate, it is cut to a proper size, and is wrapped or packaged.

The palonosetron oral transmucosal film or patch of the present invention has a length of about 1-4 cm, width about 1-4 cm; preferably a length of about 2-3 cm, and width about 1.5-2.5 cm.

The pH of the pharmaceutical composition may be inherently provided by the excipients present in the formulation; alternatively, a pH adjustment agent may be employed. A pH adjustment agent such as a buffer or a simple acid can be added to the pharmaceutical composition to maintain the pH to 5-8. Suitable acids include organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and mixtures thereof. The amount of a pH adjusting agent is in general 0.1-10% or 0.5-2%.

To increase shelf-life, the pharmaceutical may optionally include a microbial preservative. Any preservative which does not adversely interact with the active palonosetron or any of the excipients may be employed. Preferred preservatives include ethanol, benzyl alcohol, phenol, phenoxyethanol, phenylethyl alcohol, chlorobutanol, benzalkonium chloride, benzethonium chloride, benzoic acid, bronopol, butyl-paraben, cetrimide, chlorhexidine, chlorocresol, cresol, ethylparaben, glycerin, imidurea, methylparaben, phenyl mercuric borate, phenylmercuric nitrate, propylene glycol, propyl-paraben, sorbic acid, thiomersal, or a mixture thereof. The amount of preservative may range, for example, from about 0.01-10%, or 0.05-2% (w/v).

The present invention provides a method for administering palonosetron to a subject. The method comprises identifying a subject in need thereof, and administering to the buccal mucosa or sublingual mucosa of the subject the pharmaceutical composition of the present invention.

The present invention is useful in treating a subject that is a mammal, such as humans, horses, dogs and cats. The present invention is particularly useful in treating humans.

The following examples further illustrate the present invention. These examples are intended merely to be illustrative of the present invention and are not to be construed as being limiting.

EXAMPLES

Example 1: Palonosetron Hydrochloride Oral Film (Comparative Example)

Preparation: Add peppermint oil, sucralose, glycerine, palonosetron hydrochloride, hyaluronic acid, and hypromellose in a 30% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 32 mg and contains the following ingredients, which were dissolved in 288 mg of 30% aqueous ethanol solution.

| | |
|---|---|
| Palonosetron hydrochloride | 0.5 mg (1.56% w/w) |
| Hypromellose | 27.6 mg (86.14% w/w) |
| Glycerine | 0.3 mg (1% w/w) |
| Hyaluronic acid | 3.2 mg (10% w/w) |
| Peppermint oil | 0.3 mg (1% w/w) |
| Sucralose | 0.1 mg (0.3% w/w) |

The palonosetron hydrochloride oral film prepared by the above method are brittle. It shows that the plasticizer glycerine does not sufficiently improve the stretch ability of the film.

Example 2: Palonosetron Hydrochloride Oral Film

Preparation: Add peppermint oil, sucralose, polysorbate 80, palonosetron hydrochloride, hyaluronic acid, and hypromellose in a 30% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 32 mg and contains the following ingredients, which were dissolved in 288 mg of 30% aqueous ethanol solution.

| | |
|---|---|
| Palonosetron hydrochloride | 0.5 mg (1.56% w/w) |
| Hypromellose | 27.6 mg (86.14% w/w) |
| Polysorbate 80 | 0.3 mg (1% w/w) |
| Hyaluronic acid | 3.2 mg (10% w/w) |
| Peppermint oil | 0.3 mg (1% w/w) |
| Sucralose | 0.1 mg (0.3% w/w) |

The palonosetron hydrochloride oral film prepared has good flexibility, can completely dissolve in water within 30 s, and the drug dissolution rate is 76.32% after 30 min.

Example 3: Palonosetron Hydrochloride Oral Film

Preparation: Add peppermint oil, sucralose, polysorbate 80, palonosetron hydrochloride, hyaluronic acid, and hydroxypropyl cellulose (HPC) EXF in a 30% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 32 mg and contains the following ingredients, which were dissolved in 288 mg of 30% aqueous ethanol solution.

| | |
|---|---|
| Palonosetron hydrochloride | 0.5 mg (1.56% w/w) |
| HPC EXF | 27.6 mg (86.14% w/w) |
| Polysorbate 80 | 0.3 mg (1% w/w) |
| Hyaluronic acid | 3.2 mg (10% w/w) |
| Peppermint oil | 0.3 mg (1% w/w) |
| Sucralose | 0.1 mg (0.3% w/w) |

The palonosetron hydrochloride oral film prepared can completely dissolve in water within 30 s. The drug can completely leach out from the film after 30 min. The bioavailability of the film is 42.34% (refer to example 11).

Example 4: Palonosetron Hydrochloride Oral Film

Preparation: Add peppermint oil, sucralose, polysorbate 80, palonosetron hydrochloride, polyvinyl pyrrolidone (PVP), and HPC EXF in a 30% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 32 mg and contains the following ingredients, which were dissolved in 288 mg of 30% aqueous ethanol solution.

| | |
|---|---|
| Palonosetron hydrochloride | 0.5 mg (1.56% w/w) |
| HPC EXF | 27.6 mg (86.14% w/w) |
| Polysorbate 80 | 0.3 mg (1% w/w) |
| PVP | 3.2 mg (10% w/w) |
| Peppermint oil | 0.3 mg (1% w/w) |
| Sucralose | 0.1 mg (0.3% w/w) |

The palonosetron hydrochloride oral film prepared following the above composition with good flexibility can completely dissolved in water within 30 s. The drug can completely release from the film within 30 min. The bioavailability of the film is 83.70% (refer to Example 10).

Example 5: Palonosetron Hydrochloride Oral Film

Preparation: Add peppermint oil, sucralose, polysorbate 80, palonosetron hydrochloride, PVP, HPC EXF and hypromellose in a 30% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 32 mg and contains the following ingredients, which were dissolved in 288 mg of 20% aqueous ethanol solution.

| Palonosetron hydrochloride | 0.5 mg (1.56% w/w) |
| HPC EXF | 7.4 mg (23.14% w/w) |
| Hypromellose | 12.8 mg (40% w/w) |
| Polysorbate 80 | 2.56 mg (8% w/w) |
| PVP | 8 mg (25% w/w) |
| Peppermint oil | 0.64 mg (2% w/w) |
| Sucralose | 0.1 mg (0.3% w/w) |

The palonosetron hydrochloride oral film prepared has a good flexibility and can completely dissolve in water within 30 seconds. The drug can completely release from the film within 30 minutes. The bioavailability of the film is 81.41% (refer to Example 10).

Example 6: Palonosetron Hydrochloride Oral Film

Preparation: Add peppermint oil, sucralose, polysorbate 80, palonosetron hydrochloride, PVP, and HPC EXF in a 30% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 32 mg and contains the following ingredients, which were dissolved in 288 mg of 30% aqueous ethanol solution.

| Palonosetron hydrochloride | 0.5 mg (1.56% w/w) |
| HPC HXF | 18 mg (56.14% w/w) |
| Polysorbate 80 | 0.3 mg (1% w/w) |
| PVP | 12.8 mg (40% w/w) |
| Peppermint oil | 0.3 mg (1% w/w) |
| Sucralose | 0.1 mg (0.3% w/w) |

The palonosetron hydrochloride oral film prepared has a good flexibility and can completely dissolve in water within 50 seconds, and the drug dissolution rate is 81.32% in 30 minutes. However, the bioavailability of the film is 40.39% (refer to example 11).

Example 7: Palonosetron Hydrochloride Oral Film

Preparation: Add peppermint oil, sucralose, polysorbate 80, palonosetron hydrochloride, sodium carboxymethyl cellulose (CMC-Na), and HPC EXF in a 40% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 32 mg and contains the following ingredients, which were dissolved in 288 mg of 40% aqueous ethanol solution.

| Palonosetron hydrochloride | 0.5 mg (1.56% w/w) |
| HPC EXF | 27.82 mg (86.94% w/w) |
| Polysorbate 80 | 1.6 mg (5% w/w) |
| CMC-Na | 1.6 mg (5% w/w) |
| Peppermint oil | 0.16 mg (0.5% w/w) |
| Sucralose | 0.32 mg (1% w/w) |

The palonosetron hydrochloride oral film prepared has a good flexibility and can completely dissolve in water within 30 seconds. The drug can completely release from the film within 30 minutes. The bioavailability of the film is 80.52% (refer to example 11).

Example 8: Palonosetron Hydrochloride Oral Film

Preparation: Add menthol, sucralose, polysorbate 80, palonosetron hydrochloride, PVP, and HPC EXF in a 30% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 32 mg and contains the following ingredients, which were dissolved in 288 mg of 30% aqueous ethanol solution.

| Palonosetron hydrochloride | 8 mg (25% w/w) |
| HPC HXF | 16 mg (50% w/w) |
| Polysorbate 80 | 2.56 mg (8% w/w) |
| PVP | 4.8 mg (15% w/w) |
| Menthol | 0.32 mg (1% w/w) |
| Sucralose | 0.32 mg (1% w/w) |

The palonosetron hydrochloride oral film prepared has a good flexibility and can completely dissolve in water within 30 seconds. The drug can completely release from the film within 30 minutes. The bioavailability of the film is 79.09% (refer to Example 12).

Example 9: Palonosetron Hydrochloride Oral Film

Preparation: Add peppermint oil, sucralose, polysorbate 80, palonosetron hydrochloride, CMC-Na, and HPC EXF in a 30% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 32 mg and contains the following ingredients, which were dissolved in 288 mg of 50% aqueous ethanol solution.

| Palonosetron hydrochloride | 0.5 mg (1.56% w/w) |
|---|---|
| HPC EXF | 27.82 mg (86.94% w/w) |
| Polysorbate 80 | 1.6 mg (5% w/w) |
| CMC-Na | 1.6 mg (5% w/w) |
| Peppermint oil | 0.16 mg (0.5% w/w) |
| Sucralose | 0.32 mg (1% w/w) |

The film forming solution prepared in 50% ethanol aqueous solution is turbid and opaque. The film formed has many particles in the film and thus are not acceptable.

Example 10: Bioavailability of Palonosetron Hydrochloride

Beagle dogs were administered (i) the palonosetron hydrochloride oral film of Example 4 or 5 by mucous membrane administration, and (ii) the palonosetron hydrochloride injection solution by intravenous administration at a single dose of 0.05 mg/kg. Blood samples were collected, via heparin-containing tubes at 0, 2, 5, 15, 30 min, and 1, 2, 3, 4, 8 and 24 hours after dosing. The palonosetron hydrochloride concentrations in plasma were determined by HPLC-MS-MS and the bioavailability calculated. As show in Table 1, the bioavailability of each Examples 4 and 5 was 83.70% and 81.41%, respectively.

TABLE 1

Comparison the bioavailability of palonosetron hydrochloride oral film with different film-forming agents

| Pharmacokinetic parameter | Injection | Example 4 | Example 5 |
|---|---|---|---|
| Mean $T_{max}$ (h) | 0.08 | 0.5 | 0.5 |
| Mean $C_{max}$ (ng/ml) | 20.63 | 12.06 | 11.26 |
| Mean $T^{1/2}$ (h) | 0.91 | 1.32 | 1.51 |
| Mean $AUC_{last}$ (hr * ng/ml) | 21.19 | 17.66 | 17.25 |
| Absolute bioavailability % | — | 83.70 | 81.41 |

Example 11: Bioavailability of Palonosetron Hydrochloride

Beagle dogs were administered (i) the palonosetron hydrochloride oral film of Example 3, 4, 6, or 7 by mucous membrane administration, and (ii) the palonosetron hydrochloride injection solution by intravenous administration at a single dose of 0.05 mg/kg. Blood samples were collected, via heparin-containing tubes at 0, 2, 5, 15, 30 min, and 1, 2, 3, 4, 8 and 24 hours after dosing. The palonosetron hydrochloride concentrations in plasma were determined by HPLC-MS-MS and the bioavailability calculated. As show in Table 2, the bioavailability of each Example 3, 4, 6 and 7 was 42.34%, 83.70%, 40.39% and 80.52%, respectively.

TABLE 2

Comparison the bioavailability of palonosetron hydrochloride oral film with different adhesive agents

| Pharmacokinetic parameter | Injection | Exam 3 | Exam 4 | Exam 6 | Exam 7 |
|---|---|---|---|---|---|
| Mean $T_{max}$ (h) | 0.08 | 0.5 | 0.5 | 0.5 | 0.5 |
| Mean $C_{max}$ (ng/ml) | 20.63 | 10.06 | 12.06 | 11.345 | 12.32 |
| Mean $T^{1/2}$ (h) | 0.91 | 1.32 | 1.32 | 1.185 | 1.45 |
| Mean $AUC_{last}$ (hr * ng/ml) | 21.19 | 8.97 | 17.66 | 8.56 | 17.06 |
| Absolute bioavailability % | — | 42.34 | 83.70 | 40.39 | 80.52 |

Example 12: Bioavailability of Palonosetron Hydrochloride

Beagle dogs were (i) administered the palonosetron hydrochloride oral film of Example 4 at 0.05 mg/kg or example 8 at 0.8 mg/kg by mucous membrane administration, and (ii) the palonosetron hydrochloride injection solution by intravenous administration at a single dose of 0.05 mg/kg. Blood samples were collected, via heparin-containing tubes at 0, 2, 5, 15, 30 min, and 1, 2, 3, 4, 8 and 24 hours after dosing. The palonosetron hydrochloride concentrations in plasma were determined by HPLC-MS-MS and the bioavailability calculated. As shown in Table 3, the bioavailability of Example 4 and 8 were 83.70% and 79.09%, respectively.

TABLE 3

Comparison the bioavailability of palonosetron hydrochloride oral film with different penetration enhancing agents

| Pharmacokinetic parameter | Injection | Example 4 | Example 8 |
|---|---|---|---|
| Mean $T_{max}$ (h) | 0.08 | 0.5 | 0.75 |
| Mean $C_{max}$ (ng/ml) | 20.63 | 12.06 | 79.05 |
| Mean $T^{1/2}$ (h) | 0.91 | 1.32 | 2.02 |
| Mean $AUC_{last}$ (hr * ng/ml) | 21.19 | 17.66 | 268.15 |
| Absolute bioavailability % | — | 83.70 | 79.09 |

Example 13: Palonosetron Hydrochloride Oral Film

Preparation: Add menthol, sucralose, polysorbate 80, palonosetron hydrochloride, PVP, HPC EXF, and CMC-Na in a 30% aqueous ethanol solution in a vial and stir the vial until it is completely dissolved. The weight ratio of each component is indicated below. Set aside or vacuum to remove air bubbles. Coat the defoamed film solution on the conveyor belt evenly and dry up at the temperature of about 55° C. to 80° C. The aqueous ethanol solution is evaporated after drying. When the film is formed, cut the film into a suitable size and shape, and immediately wrap or bag each piece.

Each piece of film weighs 64 mg and contains the following ingredients, which were dissolved in 576 mg of 30% aqueous ethanol solution.

| Palonosetron hydrochloride | 10 mg (15.63% w/w) |
|---|---|
| HPC EXF | 45.68 mg (71.37% w/w) |
| Polysorbate 80 | 0.64 mg (1% w/w) |
| CMC-Na | 6.4 mg (10% w/w) |
| Menthol | 0.64 mg (1% w/w) |
| Sucralose | 0.64 mg (1% w/w) |

The palonosetron hydrochloride oral film prepared has a good flexibility and can completely dissolve in water within 90 seconds. The drug can completely release from the film within 45 minutes. The bioavailability of the film is 70.32% (determined by the same protocol as shown in Example 11).

Example 14. Summary of Data

Table 4 below summarizes the results of Examples 1-9, and 13. The results in each column are shown as weight % of the film.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications can be made therein without departing from the scope of the present invention as set forth in the claims. To particularly point out and distinctly claim the subject matter regarded as invention, the following claims conclude this specification.

TABLE 4

Summary of Data

| | % | Exam 1 | Exam 2 | Exam 3 | Exam 4 | Exam 5 | Exam 6 | Exam 7 | Exam 8 | Exam 9 | Exam 13 |
|---|---|---|---|---|---|---|---|---|---|---|---|
| Drug | Palonosetron | 1.6 | 1.6 | 1.6 | 1.6 | 1.6 | 1.6 | 1.6 | 25 | 1.6 | 15.6 |
| Film Material | hydromellose | 86.1 | 86.1 | | | 40 | | | | | |
| Film Material | HPCEXF | | | 86.1 | 86.1 | 23.1 | 56.1 | 86.9 | 50 | 86.9 | 71.4 |
| Plasticizer | Glycerine | 1 | | | | | | | | | |
| Plasticizer | Polysorbate 80 | | 1 | 1 | 1 | 8 | 1 | 5 | 8 | 5 | 1 |
| Adhesive | Hyaluronic acid | 10 | 10 | 10 | | | | | | | |
| Adhesive | CMC-Na | | | | | | | | 5 | 5 | 10 |
| Adhesive | PVP | | | | 10 | 25 | 40 | | 15 | | |
| Penetration enhancer | Peppermint oil | 1 | 1 | 1 | 1 | 2 | 1 | 0.5 | | 0.5 | |
| Penetration enhancer | Menthol | | | | | | | | 1 | | 1 |
| Flavoring | Sucralose | 0.3 | 0.3 | 0.3 | 0.3 | 0.3 | 0.3 | 1 | 1 | 1 | 1 |
| Aqueous solution in preparation | Ethanol (ET) | 30% ET | 30% ET | 30% ET | 30% ET | 20% ET | 30% ET | 40% ET | 30% ET | 50% ET | 30% ET |
| Bioavailability | | | | 42.34 | 83.7 | 81.4 | 40.4 | 80.5 | 79.1 | | 70.3 |
| Water solubility | | | 100% in 30 s | 100% in 30 s | 100% in 30 s | 100% in 30 s | 100% in 50 s | 100% in 30 s | 100% in 30 s | | 100% in 90 s |
| Film Formed | | brittle | flexible | flexible | flexible | flexible | flexible | flexible | flexible | many particles | flexible |

What is claimed is:

1. A pharmaceutical composition comprising 0.05-35% (w/w) of palonosetron or a pharmaceutically acceptable salt thereof, 40-90% of one or more film forming agents, 1-10% (w/w) of one or more plasticizers, 5-25% (w/v) of one or more adhesive agents, and 0.1-5% of one or more penetration enhancing agents, wherein the plasticizer is polysorbate, the penetration enhancement agent is selected from the group consisting of: peppermint oil, menthol, sodium lauryl sulfate, and any combination thereof, and the adhesive agent is polyvinyl pyrrolidone, sodium carboxymethyl cellulose polycarbophil, or carbomer.

2. The pharmaceutical composition according to claim 1, which is in a film format in a weight about 10-80 mg.

3. The pharmaceutical composition according to claim 1, wherein the film forming agent is selected from the group consisting of: hydroxypropyl cellulose, hypromellose, xanthan gum, pectin, polyethylene oxide, sodium alginate, and chitosan.

4. The pharmaceutical composition according to claim 1, wherein the film forming agent is hydroxypropyl cellulose, hypromellose, or the combination thereof.

5. The pharmaceutical composition according to claim 1, wherein the plasticizer is polysorbate 80, polysorbate 20, or the combination thereof.

6. The pharmaceutical composition according to claim 1, wherein the penetration enhancement agent is peppermint oil, menthol, or the combination thereof.

7. The pharmaceutical formulation according to claim 1, further comprising one or more flavor enhancing agents selected from the group consisting of: sucralose, sucrose, glucose, sodium saccharin, fructose, xylitol, stevia, aspartame, neotame and acesulfame potassium.

8. The pharmaceutical formulation according to claim 7, wherein the flavor enhancing agent is sucralose in an amount about 0.01-2.5%.

9. An aqueous pharmaceutical composition comprising about 10% of the pharmaceutical composition of claim 1, about 10-40% ethanol, and water.

10. A method for preparing the pharmaceutical composition of claim 2, comprising the steps of:
   a. adding the palonosetron, the film-forming materials, the plasticizers, the adhesive agents, the penetration enhancers, and optionally flavoring agents in a vial containing an aqueous organic solution, stirring the vial until it is completely dissolved, and removing any air bubbles to form a film solution;
   b. coating the film solution of (a) on a substrate and drying the film solution to form a film; and
   c. removing the film from the substrate.

11. The method according to claim 10, wherein the aqueous organic solution comprising 10-40% of an organic solvent.

12. The method according to claim 11, wherein the organic solvent is ethanol.

13. A method for administering palonosetron to a subject, comprising the steps of:
   administering to the buccal mucosa or sublingual mucosa of a subject in need thereof the pharmaceutical composition of claim 2.

14. The method according to claim 11, wherein the organic solvent is ethanol, isopropanol, ethyl acetate, t-butanol, or any mixture thereof.

* * * * *